US012793412B2

(12) United States Patent
Grundhoefer et al.

(10) Patent No.: US 12,793,412 B2
(45) Date of Patent: Nov. 10, 2026

(54) METHOD AND DEVICE FOR HEALTH MONITORING

(71) Applicant: Apple Inc., Cupertino, CA (US)

(72) Inventors: Anselm Grundhoefer, Cupertino, CA (US); Pedro Manuel Da Silva Quelhas, Sunnyvale, CA (US); Phillip N. Smith, Sunnyvale, CA (US); Omar Elafifi, Oakland, CA (US); Eshan Verma, Mountain View, CA (US); Daniele Casaburo, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/599,654

(22) Filed: Mar. 8, 2024

(65) Prior Publication Data

US 2024/0212346 A1 Jun. 27, 2024

Related U.S. Application Data

(63) Continuation of application No. 16/902,528, filed on Jun. 16, 2020, now Pat. No. 11,961,290.
(Continued)

(51) Int. Cl.

| | |
|---|---|
| ***G06V 20/20*** | (2022.01) |
| ***A61B 5/00*** | (2006.01) |
| ***A61B 5/0205*** | (2006.01) |
| ***A61B 5/024*** | (2006.01) |
| ***A61B 5/08*** | (2006.01) |
| ***A61B 5/11*** | (2006.01) |
| ***A61B 5/16*** | (2006.01) |
| ***G06F 3/147*** | (2006.01) |

(52) U.S. Cl.
CPC ............ *G06V 20/20* (2022.01); *A61B 5/0077* (2013.01); *A61B 5/02055* (2013.01); *A61B 5/1124* (2013.01); *A61B 5/163* (2017.08); *A61B 5/444* (2013.01); *A61B 5/4803* (2013.01); *A61B 5/4833* (2013.01); *A61B 5/6803* (2013.01); *A61B 5/7445* (2013.01); *G06F 3/147* (2013.01); *A61B 5/024* (2013.01); *A61B 5/0816* (2013.01); *A61B 5/082* (2013.01)

(58) Field of Classification Search
None
See application file for complete search history.

(56) References Cited

U.S. PATENT DOCUMENTS 8,963,805 B2 * 2/2015 Sugden .................... G06T 7/12
345/8
9,299,013 B1 * 3/2016 Curlander ............. G06V 40/20
(Continued)

*Primary Examiner* — Gelek W Topgyal
(74) *Attorney, Agent, or Firm* — Fernando & Partners, LLP

(57) ABSTRACT

In one implementation, a method of remedying a medical impairment of a user is performed by a device including a processor, non-transitory memory, one or more biometric sensors, an image sensor, and a display. The method includes detecting, based on data from at least one of the image sensor and the one or more biometric sensors, a medical impairment of a user of the head-mounted device from a plurality of potential medical impairments associated with a plurality of remedies. The method includes selecting, from the plurality of remedies, a remedy of the medical impairment of the user. The method includes controlling the display to effect the remedy of the medical impairment of the user.

20 Claims, 14 Drawing Sheets

Related U.S. Application Data

(60) Provisional application No. 62/905,653, filed on Sep. 25, 2019.

(56) References Cited

U.S. PATENT DOCUMENTS

| | | | | | |
|---|---|---|---|---|---|
| 9,486,720 | B2 * | 11/2016 | Hanina | A61B 5/1128 | |
| 10,439,657 | B2 | 10/2019 | Pillai et al. | | |
| 10,497,161 | B1 | 12/2019 | Jones et al. | | |
| 10,579,749 | B1 * | 3/2020 | Davis | G06F 30/20 | |
| 11,094,124 | B1 * | 8/2021 | Schweinfurth | G16H 40/20 | |
| 11,169,606 | B2 | 11/2021 | Byerley | | |
| 11,235,243 | B2 * | 2/2022 | Osman | G06F 3/013 | |
| 11,581,099 | B1 * | 2/2023 | Rufo | G16H 20/13 | |
| 2003/0174049 | A1 | 9/2003 | Beigel et al. | | |
| 2005/0085343 | A1 | 4/2005 | Burrows et al. | | |
| 2010/0042430 | A1 * | 2/2010 | Bartfeld | G06Q 99/00 | 705/2 |
| 2013/0293688 | A1 | 11/2013 | Benson et al. | | |
| 2014/0160157 | A1 * | 6/2014 | Poulos | G06F 3/011 | 345/633 |
| 2014/0278648 | A1 * | 9/2014 | Bussey | G06Q 10/063114 | 705/7.15 |
| 2015/0109442 | A1 * | 4/2015 | Derenne | H04N 7/185 | 348/143 |
| 2015/0223705 | A1 * | 8/2015 | Sadhu | A61B 5/0006 | 600/595 |
| 2016/0044276 | A1 | 2/2016 | Shearman et al. | | |
| 2016/0104451 | A1 | 4/2016 | Sahin | | |
| 2016/0124501 | A1 * | 5/2016 | Lam | G06F 3/017 | 345/156 |
| 2016/0335800 | A1 * | 11/2016 | DeStories | G06F 3/04883 | |
| 2016/0342767 | A1 * | 11/2016 | Narasimhan | G16H 40/63 | |
| 2017/0270362 | A1 | 9/2017 | Barnehama et al. | | |
| 2017/0326333 | A1 | 11/2017 | Giap et al. | | |
| 2018/0003982 | A1 | 1/2018 | Burns et al. | | |
| 2018/0004478 | A1 | 1/2018 | Chen | | |
| 2018/0256115 | A1 | 9/2018 | Campbell et al. | | |
| 2018/0349561 | A1 * | 12/2018 | Lecamus | G16H 20/13 | |
| 2019/0087554 | A1 | 3/2019 | Fish et al. | | |
| 2019/0243599 | A1 * | 8/2019 | Rochford | G06F 3/147 | |
| 2020/0004016 | A1 * | 1/2020 | Gross | G02B 27/017 | |
| 2020/0090809 | A1 | 3/2020 | Baughman et al. | | |
| 2020/0124845 | A1 | 4/2020 | Smith et al. | | |
| 2020/0143943 | A1 | 5/2020 | Nelson et al. | | |
| 2021/0019953 | A1 | 1/2021 | Pekelny et al. | | |
| 2021/0282736 | A1 * | 9/2021 | Stamatopoulos | A61B 5/725 | |
| 2022/0141379 | A1 * | 5/2022 | Lei | G02B 7/28 | 348/348 |
| 2022/0226600 | A1 * | 7/2022 | Perera | G06T 19/006 | |
| 2023/0238098 | A1 * | 7/2023 | Langan | G16H 20/10 | 345/156 |

* cited by examiner

METHOD AND DEVICE FOR HEALTH MONITORING

CROSS-REFERENCE TO RELATED APPLICATIONS

This application is a continuation of U.S. patent application Ser. No. 16/902,528, filed on Jun. 16, 2020, which claims priority to U.S. Provisional Patent App. No. 62/905,653, filed on Sep. 25, 2019, which are both hereby incorporated by reference in their entirety.

TECHNICAL FIELD

The present disclosure generally relates to health monitoring and, in particular, to systems, methods, and devices for monitoring the health of a user in a computer-generated reality environment.

BACKGROUND

A physical environment refers to a physical world that people can sense and/or interact with without aid of electronic systems. Physical environments, such as a physical park, include physical articles, such as physical trees, physical buildings, and physical people.

People can directly sense and/or interact with the physical environment, such as through sight, touch, hearing, taste, and smell.

In contrast, a computer-generated reality (CGR) environment refers to a wholly or partially simulated environment that people sense and/or interact with via an electronic system. In CGR, a subset of a person's physical motions, or representations thereof, are tracked, and, in response, one or more characteristics of one or more virtual objects simulated in the CGR environment are adjusted in a manner that comports with at least one law of physics. For example, a CGR system may detect a person's head turning and, in response, adjust graphical content and an acoustic field presented to the person in a manner similar to how such views and sounds would change in a physical environment. In some situations (e.g., for accessibility reasons), adjustments to characteristic(s) of virtual object(s) in a CGR environment may be made in response to representations of physical motions (e.g., vocal commands).

A person may sense and/or interact with a CGR object using any one of their senses, including sight, sound, touch, taste, and smell. For example, a person may sense and/or interact with audio objects that create 3D or spatial audio environment that provides the perception of point audio sources in 3D space. In another example, audio objects may enable audio transparency, which selectively incorporates ambient sounds from the physical environment with or without computer-generated audio. In some CGR environments, a person may sense and/or interact only with audio objects.

Examples of CGR include virtual reality and mixed reality.

A virtual reality (VR) environment refers to a simulated environment that is designed to be based entirely on computer-generated sensory inputs for one or more senses. A VR environment comprises a plurality of virtual objects with which a person may sense and/or interact. For example, computer-generated imagery of trees, buildings, and avatars representing people are examples of virtual objects. A person may sense and/or interact with virtual objects in the VR environment through a simulation of the person's presence within the computer-generated environment, and/or through a simulation of a subset of the person's physical movements within the computer-generated environment.

In contrast to a VR environment, which is designed to be based entirely on computer-generated sensory inputs, a mixed reality (MR) environment refers to a simulated environment that is designed to incorporate sensory inputs from the physical environment, or a representation thereof, in addition to including computer-generated sensory inputs (e.g., virtual objects). On a virtuality continuum, a mixed reality environment is anywhere between, but not including, a wholly physical environment at one end and virtual reality environment at the other end.

In some MR environments, computer-generated sensory inputs may respond to changes in sensory inputs from the physical environment. Also, some electronic systems for presenting an MR environment may track location and/or orientation with respect to the physical environment to enable virtual objects to interact with real objects (that is, physical articles from the physical environment or representations thereof). For example, a system may account for movements so that a virtual tree appears stationery with respect to the physical ground.

Examples of mixed realities include augmented reality and augmented virtuality.

An augmented reality (AR) environment refers to a simulated environment in which one or more virtual objects are superimposed over a physical environment, or a representation thereof. For example, an electronic system for presenting an AR environment may have a transparent or translucent display through which a person may directly view the physical environment. The system may be configured to present virtual objects on the transparent or translucent display, so that a person, using the system, perceives the virtual objects superimposed over the physical environment. Alternatively, a system may have an opaque display and one or more imaging sensors that capture images or video of the physical environment, which are representations of the physical environment. The system composites the images or video with virtual objects, and presents the composition on the opaque display.

A person, using the system, indirectly views the physical environment by way of the images or video of the physical environment, and perceives the virtual objects superimposed over the physical environment. As used herein, a video of the physical environment shown on an opaque display is called "pass-through video," meaning a system uses one or more image sensor(s) to capture images of the physical environment, and uses those images in presenting the AR environment on the opaque display. Further alternatively, a system may have a projection system that projects virtual objects into the physical environment, for example, as a hologram or on a physical surface, so that a person, using the system, perceives the virtual objects superimposed over the physical environment.

An augmented reality environment also refers to a simulated environment in which a representation of a physical environment is transformed by computer-generated sensory information. For example, in providing pass-through video, a system may transform one or more sensor images to impose a select perspective (e.g., viewpoint) different than the perspective captured by the imaging sensors. As another example, a representation of a physical environment may be transformed by graphically modifying (e.g., enlarging) portions thereof, such that the modified portion may be representative but not photorealistic versions of the originally captured images. As a further example, a representation of a physical environment may be transformed by graphically eliminating or obfuscating portions thereof.

An augmented virtuality (AV) environment refers to a simulated environment in which a virtual or computer-generated environment incorporates one or more sensory inputs from the physical environment. The sensory inputs may be representations of one or more characteristics of the physical environment. For example, an AV park may have virtual trees and virtual buildings, but people with faces photorealistically reproduced from images taken of physical people. As another example, a virtual object may adopt a shape or color of a physical article imaged by one or more imaging sensors. As a further example, a virtual object may adopt shadows consistent with the position of the sun in the physical environment.

There are many different types of electronic systems that enable a person to sense and/or interact with various CGR environments. Examples include head-mounted systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head-mounted system may have one or more speaker(s) and an integrated opaque display. Alternatively, a head-mounted system may be configured to accept an external opaque display (e.g., a smartphone). The head-mounted system may incorporate one or more imaging sensors to capture images or video of the physical environment, and/or one or more microphones to capture audio of the physical environment. Rather than an opaque display, a head-mounted system may have a transparent or translucent display. The transparent or translucent display may have a medium through which light representative of images is directed to a person's eyes.

The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In one implementation, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

In various implementations, a head-mounted device (HMD) including a scene camera and a display is used to present a CGR environment. The HMD can further include a variety of other sensors, including an inertial measurement unit (IMU) and or biometric sensors (such as a thermometer, a heart monitor, breathing monitor, or an electrodermal monitor). It may be desirable to effectively use the information provided by the scene camera and the sensors to monitor the health of the user of the HMD.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1A:
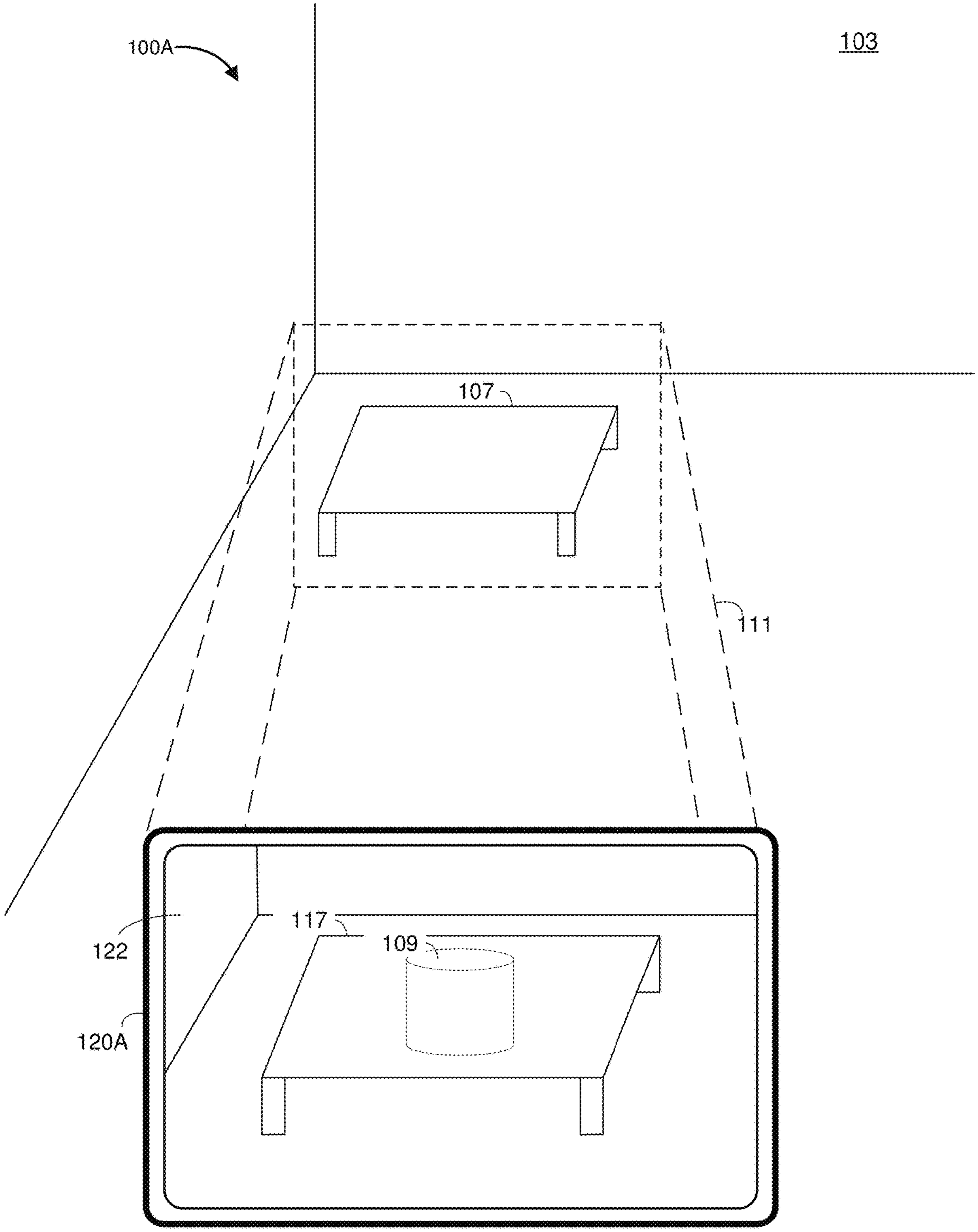
FIG. 1A is a block diagram of an example operating architecture in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for remedying a medical impairment of a user. In various implementations, a method is performed at a device including a processor, non-transitory memory, one or more biometric sensors, an image sensor, and a display. The method includes detecting, based on data from at least one of the image sensor and the one or more biometric sensors, a medical impairment of a user of the head-mounted device from a plurality of potential medical impairments associated with a plurality of remedies. The method includes selecting, from the plurality of remedies, a remedy of the medical impairment of the user. The method includes controlling the display to effect the remedy of the medical impairment of the user.

In accordance with some implementations, a device includes one or more processors, a non-transitory memory, and one or more programs; the one or more programs are stored in the non-transitory memory and configured to be executed by the one or more processors. The one or more programs include instructions for performing or causing performance of any of the methods described herein. In accordance with some implementations, a non-transitory computer readable storage medium has stored therein instructions, which, when executed by one or more processors of a device, cause the device to perform or cause performance of any of the methods described herein. In accordance with some implementations, a device includes: one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting.

Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

As noted above, in various implementations, a head-mounted device (HMD) includes, as input devices, a scene camera and a variety of other sensors, and, as an output device, a display to present a CGR environment. The wide array of information from the sensors (including the scene camera) can be used to monitor the health of the user of the HMD and the display can be used to remedy any medical impairment detected.

FIG. 1A is a block diagram of an example operating architecture 100A in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating architecture 100A includes an electronic device 120A.

In some implementations, the electronic device 120A is configured to present CGR content to a user. In some implementations, the electronic device 120A includes a suitable combination of software, firmware, and/or hardware. According to some implementations, the electronic device 120A presents, via a display 122, CGR content to the user while the user is physically present within a physical environment 103 that includes a table 107 within the field-of-view 111 of the electronic device 120A. As such, in some implementations, the user holds the electronic device 120A in his/her hand(s). In some implementations, while providing augmented reality (AR) content, the electronic device 120A is configured to display an AR object (e.g., an AR cylinder 109) and to enable video pass-through of the physical environment 103 (e.g., including a representation 117 of the table 107) on a display 122.

Figure 1B:
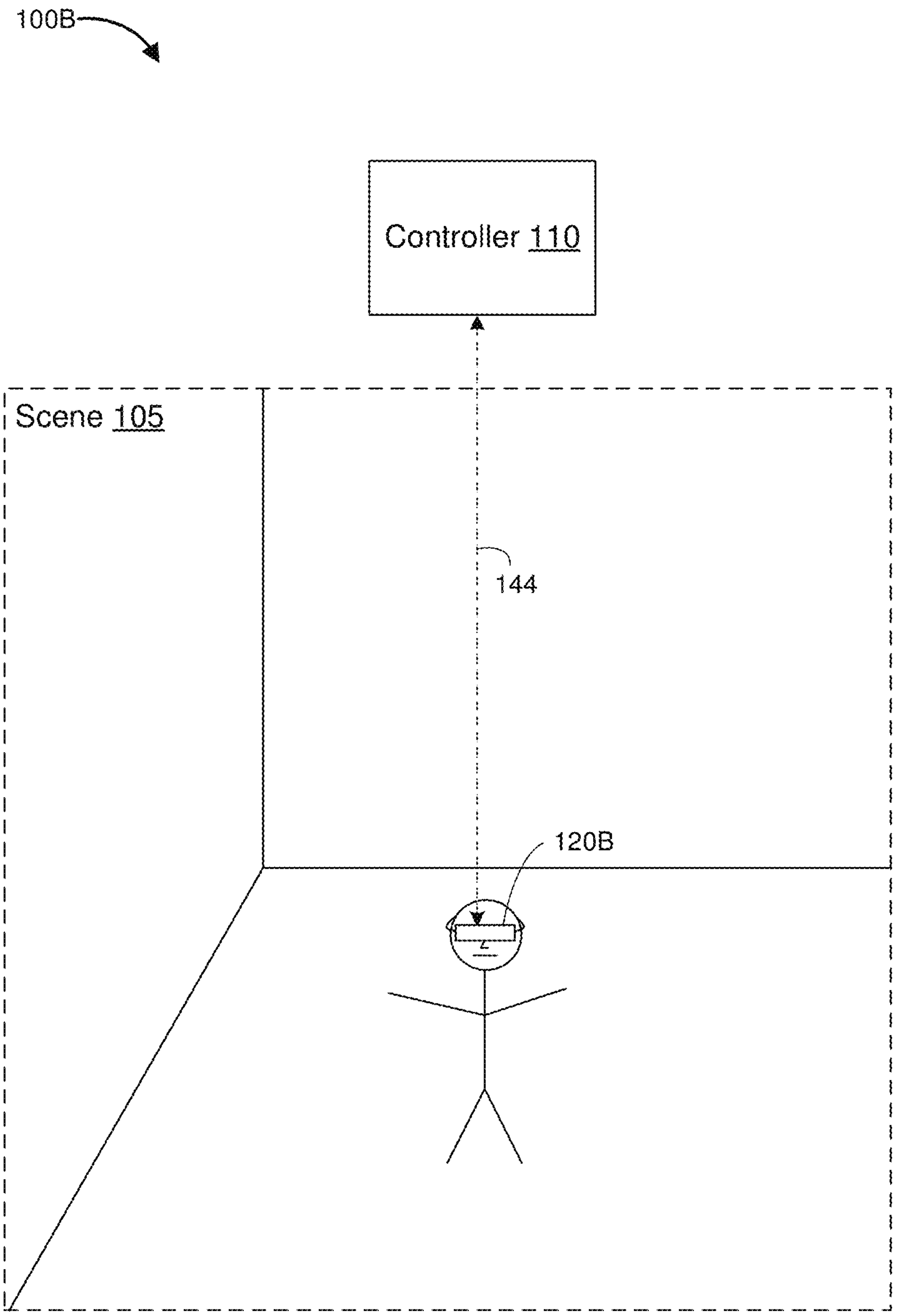
FIG. 1B is a block diagram of an example operating architecture in accordance with some implementations.

FIG. 1B is a block diagram of an example operating architecture 100B in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 100B includes a controller 110 and a head-mounted device (HMD) 120B.

In some implementations, the controller 110 is configured to manage and coordinate presentation of CGR content for the user. In some implementations, the controller 110 includes a suitable combination of software, firmware, and/or hardware. The controller 110 is described in greater detail below with respect to FIG. 2. In some implementations, the controller 110 is a computing device that is local or remote relative to the scene 105. For example, the controller 110 is a local server located within the scene 105. In another example, the controller 110 is a remote server located outside of the scene 105 (e.g., a cloud server, central server, etc.). In some implementations, the controller 110 is communicatively coupled with the HMD 120B via one or more wired or wireless communication channels 144 (e.g., BLUETOOTH, IEEE 802.11x, IEEE 802.16x, IEEE 802.3x, etc.). In another example, the controller 110 is included within the enclosure of the HMD 120B.

In some implementations, the HMD 120B is configured to present the CGR content to the user. In some implementations, the HMD 120B includes a suitable combination of software, firmware, and/or hardware. The HMD 120B is described in greater detail below with respect to FIG. 3. In some implementations, the functionalities of the controller 110 are provided by and/or combined with the HMD 120B.

According to some implementations, the HMD 120B presents CGR content to the user while the user is virtually and/or physically present within the scene 105.

In some implementations, the user wears the HMD 120B on his/her head. As such, the HMD 120B includes one or more CGR displays provided to display CGR content. For example, in various implementations, the HMD 120B encloses the field-of-view of the user. In some implementations, such as in FIG. 1A, the HMD 120B is replaced with a handheld device (such as a smartphone or tablet) configured to present CGR content, and rather than wearing the HMD 120B the user holds the device with a display directed towards the field-of-view of the user and a camera directed towards the scene 105.

In some implementations, the handheld device can be placed within an enclosure that can be worn on the head of the user. In some implementations, the HMD 120B is replaced with a CGR chamber, enclosure, or room configured to present CGR content in which the user does not wear or hold the HMD 120B.

Figure 2:
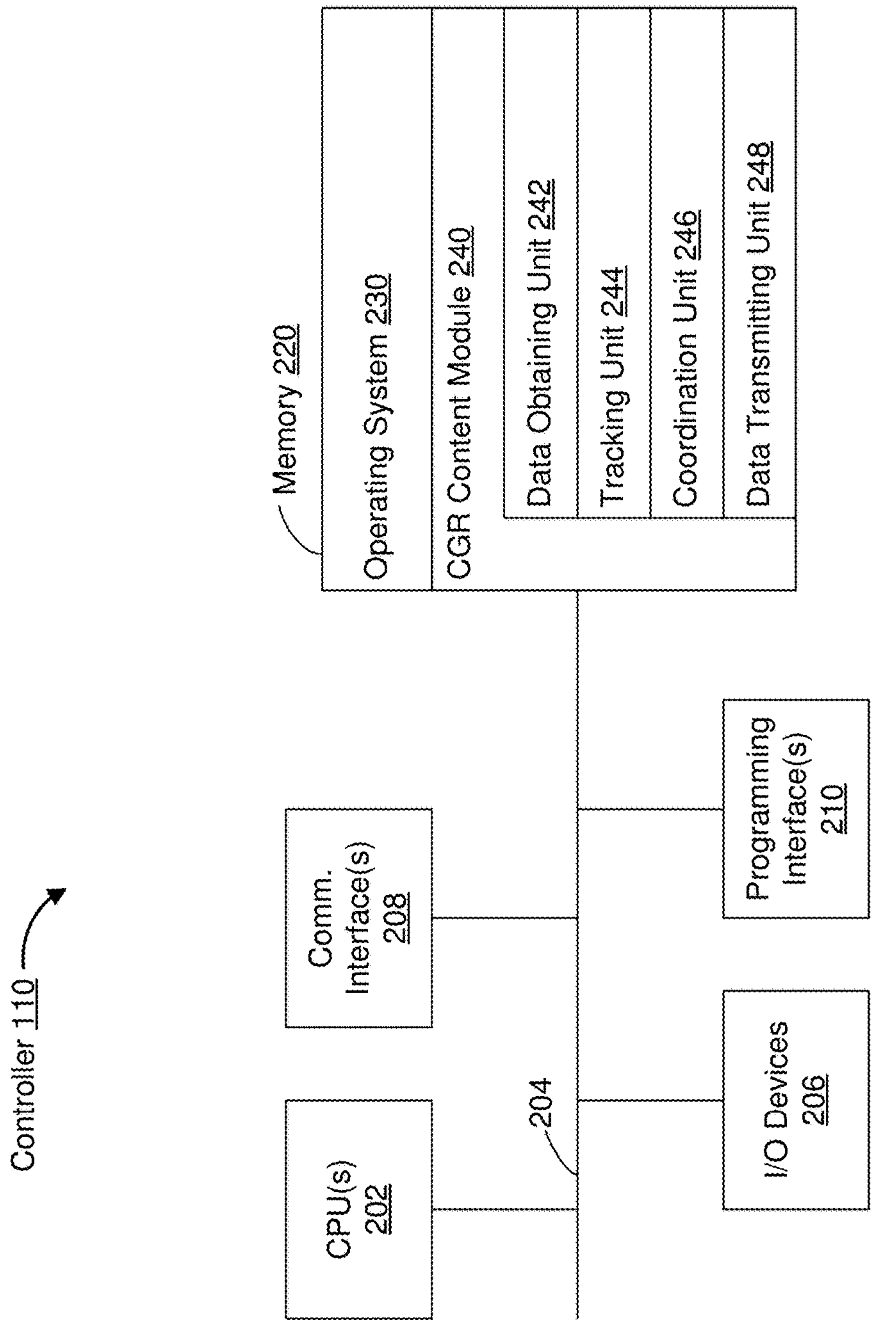
FIG. 2 is a block diagram of an example controller in accordance with some implementations.

FIG. 2 is a block diagram of an example of the controller 110 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the controller 110 includes one or more processing units 202 (e.g., microprocessors, application-specific integrated-circuits (ASICs), field-programmable gate arrays (FPGAs), graphics processing units (GPUs), central processing units (CPUs), processing cores, and/or the like), one or more input/output (I/O) devices 206, one or more communication interfaces 208 (e.g., universal serial bus (USB), FIREWIRE, THUNDERBOLT, IEEE 802.3x, IEEE 802.11x, IEEE 802.16x, global system for mobile communications (GSM), code division multiple access (CDMA), time division multiple access (TDMA), global positioning system (GPS), infrared (IR), BLUETOOTH, ZIGBEE, and/or the like type interface), one or more programming (e.g., I/O) interfaces 210, a memory 220, and one or more communication buses 204 for interconnecting these and various other components.

In some implementations, the one or more communication buses 204 include circuitry that interconnects and controls communications between system components. In some implementations, the one or more I/O devices 206 include at least one of a keyboard, a mouse, a touchpad, a joystick, one or more microphones, one or more speakers, one or more image sensors, one or more displays, and/or the like.

The memory 220 includes high-speed random-access memory, such as dynamic random-access memory (DRAM), static random-access memory (SRAM), double-data-rate random-access memory (DDR RAM), or other random-access solid-state memory devices. In some implementations, the memory 220 includes non-volatile memory, such as one or more magnetic disk storage devices, optical disk storage devices, flash memory devices, or other non-volatile solid-state storage devices. The memory 220 optionally includes one or more storage devices remotely located from the one or more processing units 202. The memory 220 comprises a non-transitory computer readable storage medium. In some implementations, the memory 220 or the non-transitory computer readable storage medium of the memory 220 stores the following programs, modules and data structures, or a subset thereof including an optional operating system 230 and a CGR content module 240.

The operating system 230 includes procedures for handling various basic system services and for performing hardware dependent tasks. In some implementations, the CGR content module 240 is configured to manage and coordinate presentation of CGR content for one or more users (e.g., a single set of CGR content for one or more users, or multiple sets of CGR content for respective groups of one or more users). To that end, in various implementations, the CGR content module 240 includes a data obtaining unit 242, a tracking unit 244, a coordination unit 246, and a data transmitting unit 248.

In some implementations, the data obtaining unit 242 is configured to obtain data (e.g., presentation data, interaction data, sensor data, location data, etc.) from at least the HMD 120B of FIG. 1B. To that end, in various implementations, the data obtaining unit 242 includes instructions and/or logic therefor, and heuristics and metadata therefor.

In some implementations, the tracking unit 244 is configured to map the scene 105 and to track the position/location of at least the HMD 120B with respect to the scene 105 of FIG. 1B. To that end, in various implementations, the tracking unit 244 includes instructions and/or logic therefor, and heuristics and metadata therefor.

In some implementations, the coordination unit 246 is configured to manage and coordinate the presentation of CGR content to the user by the HMD 120B. To that end, in various implementations, the coordination unit 246 includes instructions and/or logic therefor, and heuristics and metadata therefor.

In some implementations, the data transmitting unit 248 is configured to transmit data (e.g., presentation data, location data, etc.) to at least the HMD 120B. To that end, in various implementations, the data transmitting unit 248 includes instructions and/or logic therefor, and heuristics and metadata therefor.

Although the data obtaining unit 242, the tracking unit 244, the coordination unit 246, and the data transmitting unit 248 are shown as residing on a single device (e.g., the controller 110), it should be understood that in other implementations, any combination of the data obtaining unit 242, the tracking unit 244, the coordination unit 246, and the data transmitting unit 248 may be located in separate computing devices.

Moreover, FIG. 2 is intended more as functional description of the various features that may be present in a particular implementation as opposed to a structural schematic of the implementations described herein. As recognized by those of ordinary skill in the art, items shown separately could be combined and some items could be separated. For example, some functional modules shown separately in FIG. 2 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Figure 3:
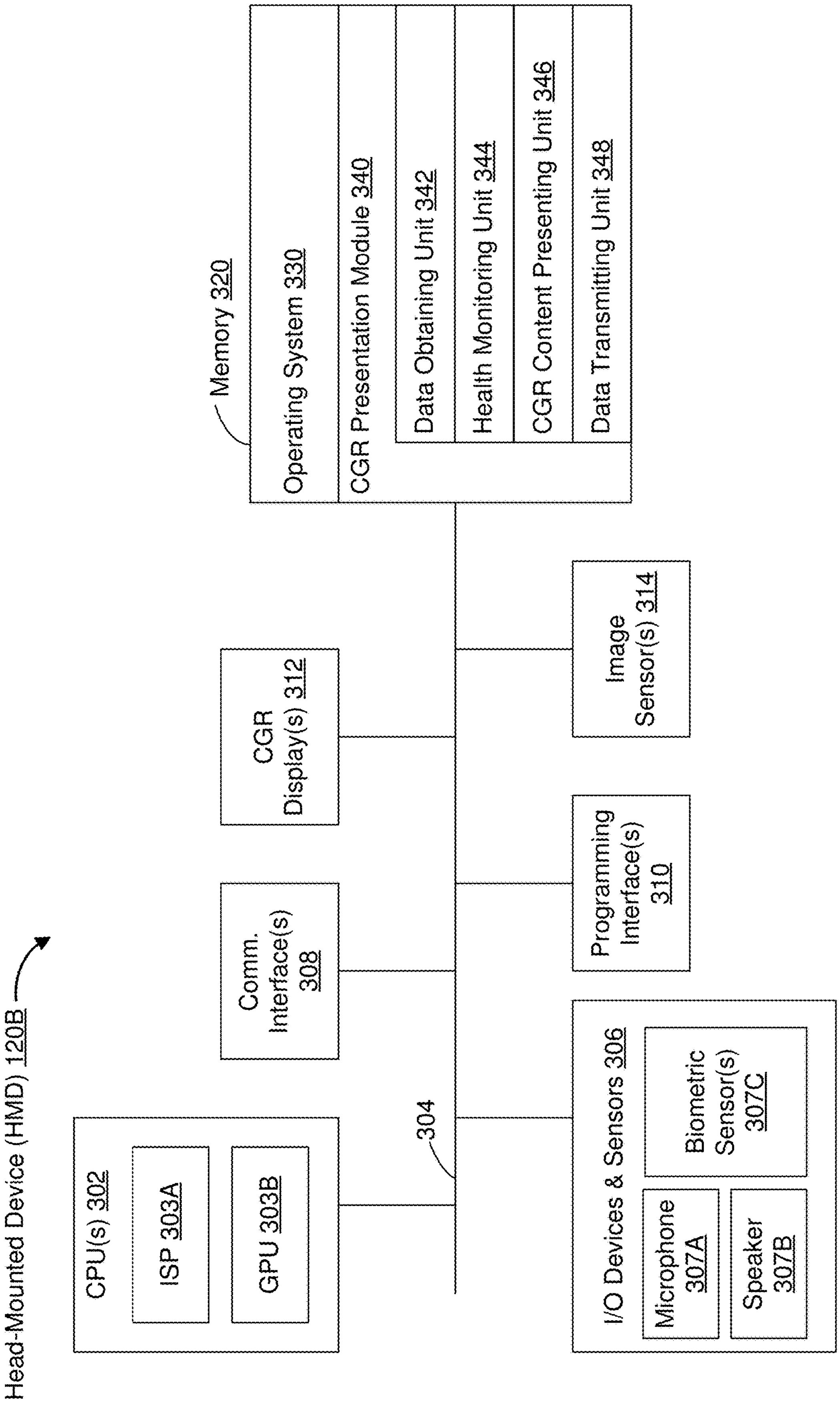
FIG. 3 is a block diagram of an example head-mounted device (HMD) in accordance with some implementations.

FIG. 3 is a block diagram of an example of the HMD 120B in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the HMD 120B includes one or more processing units 302 (e.g., microprocessors, ASICs, FPGAs, GPUs, CPUs, processing cores, and/or the like), one or more input/output (I/O) devices and sensors 306, one or more communication interfaces 308 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, and/or the like type interface), one or more programming (e.g., I/O) interfaces 310, one or more CGR displays 312, one or more interior- and/or exterior-facing image sensors 314, a memory 320, and one or more communication buses 304 for interconnecting these and various other components.

In some implementations, the one or more communication buses 304 include circuitry that interconnects and controls communications between system components. In some implementations, the one or more I/O devices and sensors 306 include at least one of an inertial measurement unit (IMU), an accelerometer, a gyroscope, an ambient temperature thermometer, one or more microphones 307A, one or more speakers 307B, one or more biometric sensors 307C (e.g., blood pressure monitor, heart rate monitor, breathing monitor, electrodermal monitor, blood oxygen sensor, blood glucose sensor, body temperature thermometer etc.), a haptics engine, one or more depth sensors (e.g., a structured light, a time-of-flight, or the like), and/or the like.

In some implementations, the one or more CGR displays 312 are configured to display CGR content to the user. In some implementations, the one or more CGR displays 312 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro-mechanical system (MEMS), and/or the like display types. In some implementations, the one or more CGR displays 312 correspond to diffractive, reflective, polarized, holographic, etc. waveguide displays. For example, the HMD 120B includes a single CGR display. In another example, the HMD 120B includes a CGR display for each eye of the user. In some implementations, the one or more CGR displays 312 are capable of presenting MR and VR content.

In some implementations, the one or more image sensors 314 are configured to obtain image data that corresponds to at least a portion of the face of the user that includes the eyes of the user (any may be referred to as an eye-tracking camera). In some implementations, the one or more image sensors 314 are configured to be forward-facing so as to obtain image data that corresponds to the scene as would be viewed by the user if the HMD 120B was not present (and may be referred to as a scene camera). The one or more image sensors 314 can include one or more RGB cameras (e.g., with a complimentary metal-oxide-semiconductor (CMOS) image sensor or a charge-coupled device (CCD) image sensor), one or more infrared (IR) cameras, one or more ultraviolet (UV) cameras, one or more event-based cameras, and/or the like. Thus, in various implementations, the one or more image sensors 314 can includes one or more cameras which sense the visible and/or IR and/or UV spectrum in one or more independent channels using filters.

In various implementations, the one or more processing units 302 includes an image signal processor (ISP) 303A and a graphics processing unit (GPU) 303B. In various implementations, the ISP 303A processes the image data received from the one or more image sensors 314. In various implementations, the ISP 303A includes one or more object detectors that detect objects, such as a hand of a user or a dose of medicine. In various implementations, the GPU 303B processes image data received from the one or more image sensors 314 to augment pass-through video of a scene to include one or more virtual objects.

The memory 320 includes high-speed random-access memory, such as DRAM, SRAM, DDR RAM, or other random-access solid-state memory devices. In some implementations, the memory 320 includes non-volatile memory, such as one or more magnetic disk storage devices, optical disk storage devices, flash memory devices, or other non-volatile solid-state storage devices. The memory 320 optionally includes one or more storage devices remotely located from the one or more processing units 302. The memory 320 comprises a non-transitory computer readable storage medium. In some implementations, the memory 320 or the non-transitory computer readable storage medium of the memory 320 stores the following programs, modules and data structures, or a subset thereof including an optional operating system 330 and a CGR presentation module 340.

The operating system 330 includes procedures for handling various basic system services and for performing hardware dependent tasks. In some implementations, the CGR presentation module 340 is configured to present CGR content to the user via the one or more CGR displays 312 and/or the I/O devices and sensors 306 (such as the one or more speakers 307B). To that end, in various implementations, the CGR presentation module 340 includes a data obtaining unit 342, a health monitoring unit 344, a CGR content presenting unit 346, and a data transmitting unit 348.

In some implementations, the data obtaining unit 342 is configured to obtain data (e.g., presentation data, interaction data, sensor data, location data, etc.) from at least the controller 110 of FIG. 1. In various implementations, the data obtaining unit 342 is configured to obtain data from the I/O devices and sensors 306. To that end, in various implementations, the data obtaining unit 342 includes instructions and/or logic therefor, and heuristics and metadata therefor.

In some implementations, the health monitoring unit 344 is configured to monitor the health of a user of the HMD 120B and to detect medical impairments of the user. To that end, in various implementations, the health monitoring unit 344 includes instructions and/or logic therefor, and heuristics and metadata therefor.

In some implementations, the CGR content presenting unit 346 is configured to present CGR content to a user. In various implementations, the CGR content presenting unit 344 controls the one or more CGR displays 312 to effect a remedy of a detected medical impairment. To that end, in various implementations, the CGR content presenting unit 346 includes instructions and/or logic therefor, and heuristics and metadata therefor.

In some implementations, the data transmitting unit 348 is configured to transmit data (e.g., presentation data, location data, etc.) to at least the controller 110. To that end, in various implementations, the data transmitting unit 348 includes instructions and/or logic therefor, and heuristics and metadata therefor.

Although the data obtaining unit 342, the health monitoring unit 344, the CGR content presenting unit 346, and the data transmitting unit 348 are shown as residing on a single device (e.g., the HMD 120B of FIG. 1B), it should be understood that in other implementations, any combination of the data obtaining unit 342, the health monitoring unit 344, the CGR content presenting unit 346, and the data transmitting unit 348 may be located in separate computing devices.

Moreover, FIG. 3 is intended more as a functional description of the various features that could be present in a particular implementation as opposed to a structural schematic of the implementations described herein. As recognized by those of ordinary skill in the art, items shown separately could be combined and some items could be separated. For example, some functional modules shown separately in FIG. 3 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

With a vast amount of biometric information from a scene camera and/or biometric sensors, an HMD is able to detect whether a user of the HMD suffers from any of a predetermined list of medical impairments. If a particular medical impairment is detected, the HMD can control the display to effect a remedy for the particular medical impairment.

Figure 4A:
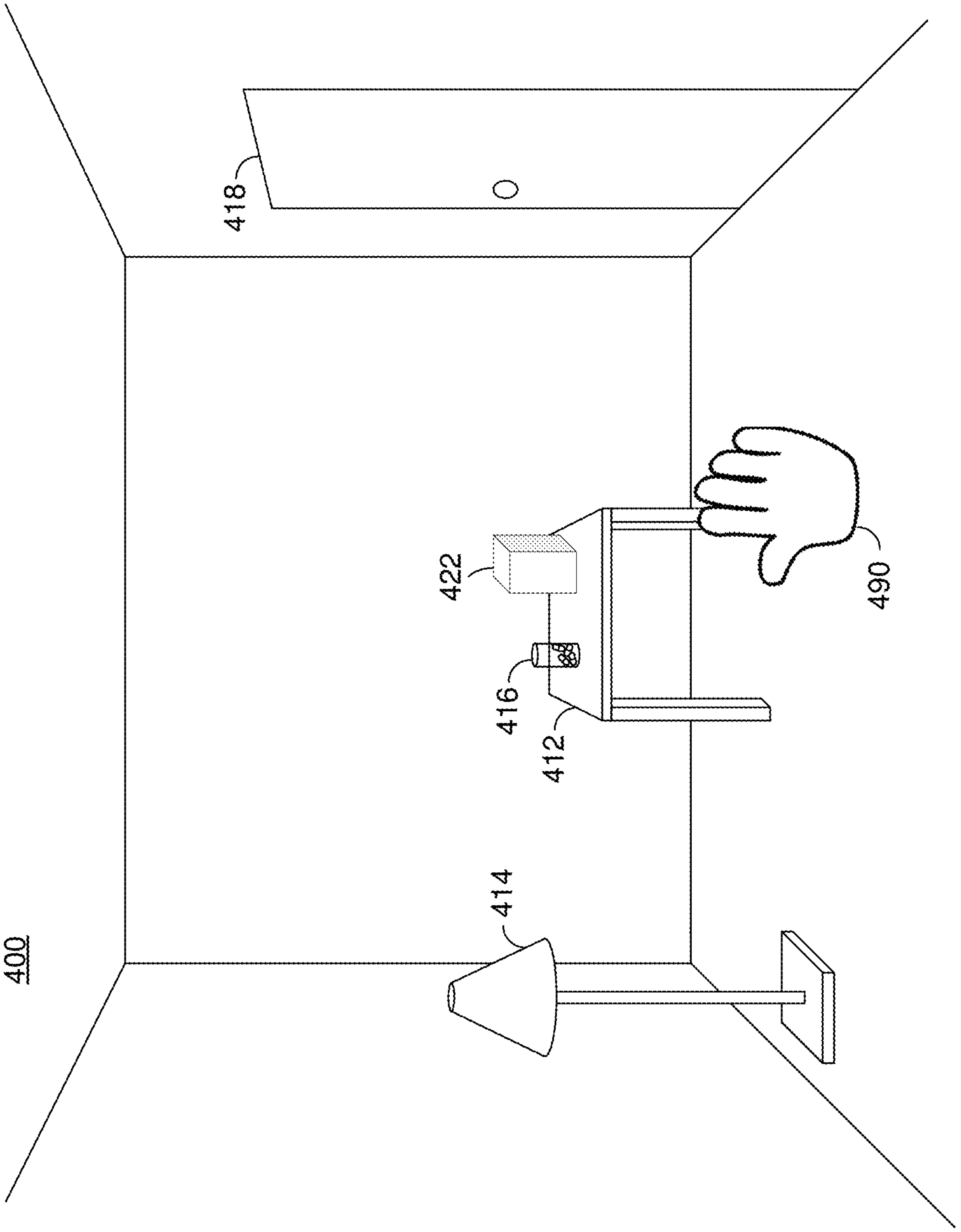
FIGS. 4A-4I illustrates a CGR environment based on a real environment surveyed by a scene camera of a device at various times.

FIG. 4A illustrates a CGR environment 400 based on a real environment surveyed by a scene camera of a device at a first time. In various implementations, the scene camera is part of a device that is worn by the user and includes a display that displays the first CGR environment 400. In various implementations, the device includes more than one scene camera. Thus, in various implementations, the user is physically present in the environment. In various implementations, the scene camera is part of remote device (such as a drone or robotic avatar) that transmits images from the scene camera to a local device that is worn by the user and includes a display that displays the CGR environment 400.

The CGR environment 400 includes a plurality of objects, including one or more real objects (e.g., a table 412, a lamp 414, a medicine bottle 416, a door 418, and the user's hand 490) and one or more virtual objects (e.g., a virtual box 422). In various implementations, each object is displayed at a location in the first CGR environment 400, e.g., at a location defined by three coordinates in a three-dimensional (3D) CGR coordinate system. Accordingly, when the user moves in the CGR environment 400 (e.g., changes either position and/or orientation), the objects are moved on the display of the HMD but retain their location in the CGR environment 400. In various implementations, certain virtual objects are displayed at locations on the display such that when the user moves in the CGR environment 400, the objects are stationary on the display on the HMD.

Figure 4B:
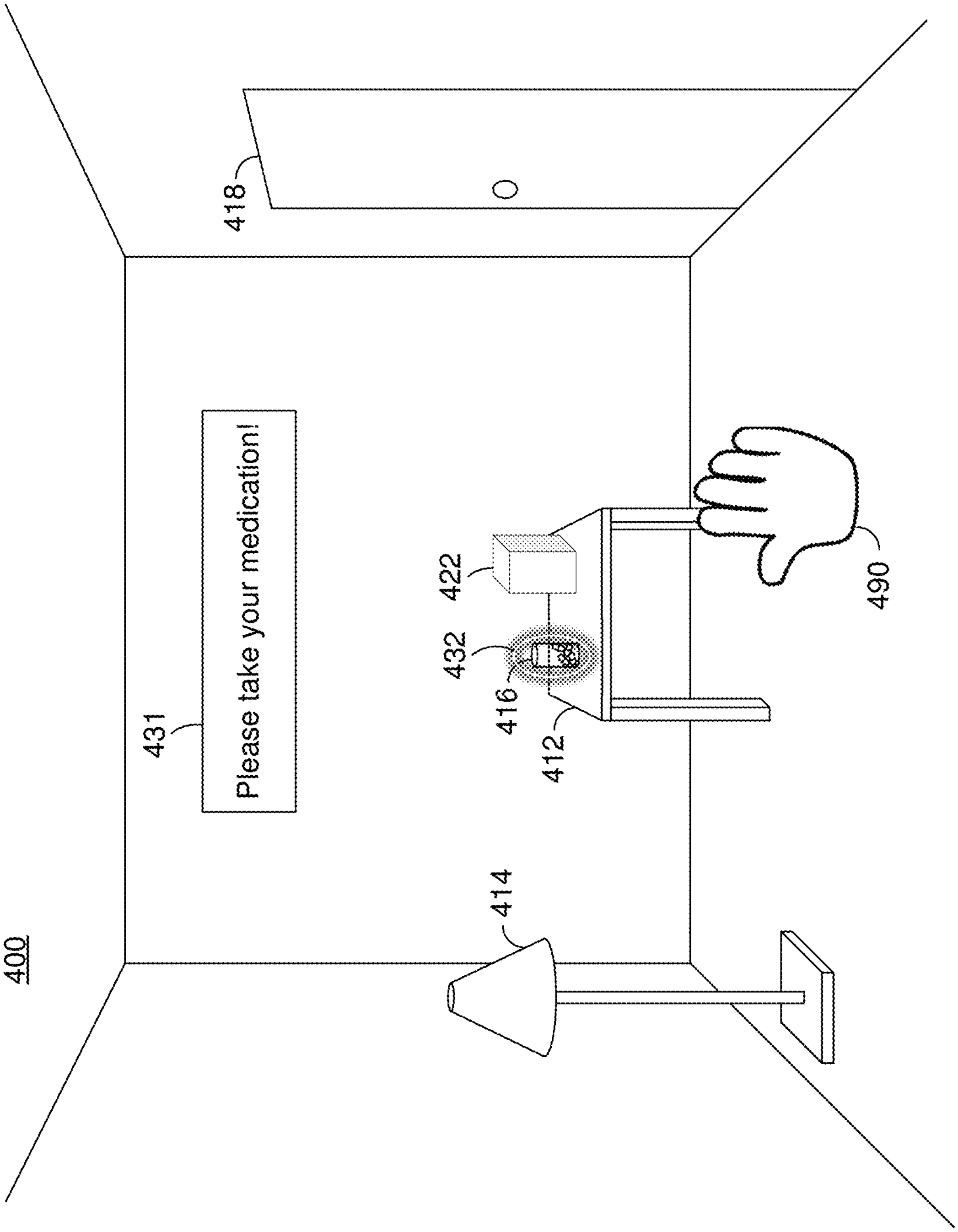

At the first time, the HMD detects that the user has failed to take a scheduled dose of medication located within the medicine bottle 416. For example, using the scene camera, the HMD did not detect the dose of medication in the hand 490 of the user prior to a time of the scheduled dose. FIG. 4B illustrates the CGR environment 400 of FIG. 4A in response to the HMD detecting that the user has failed to take a scheduled dose of medication.

FIG. 4B illustrates a CGR environment 400 of FIG. 4A at a second time. At the second time, the CGR environment 400 includes a reminder window 431 indicating that the user has not taken a scheduled dose of medication. Further, at the second time, the CGR environment includes a glow 432 directing the attention of the user to the medicine bottle 416.

Figure 4C:
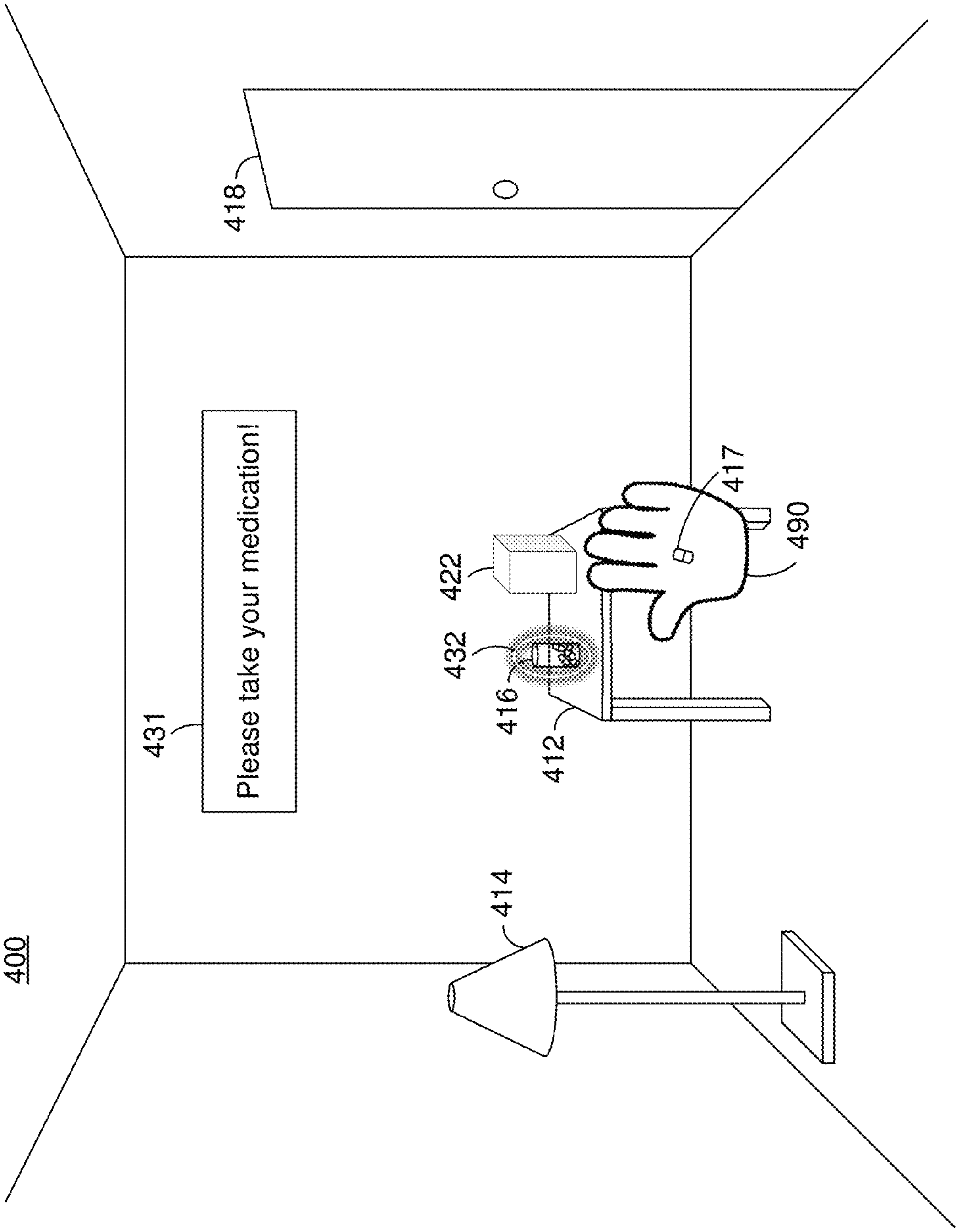

FIG. 4C illustrates the CGR environment 400 of FIG. 4A at a third time. At the third time, the user has retrieved a dose of medication 417 from the medicine bottle 416 and is holding the dose of medication 417 in the user's hand 490. At the third time, the CGR environment 400 still includes the reminder window 431 and the glow 432.

Figure 4D:
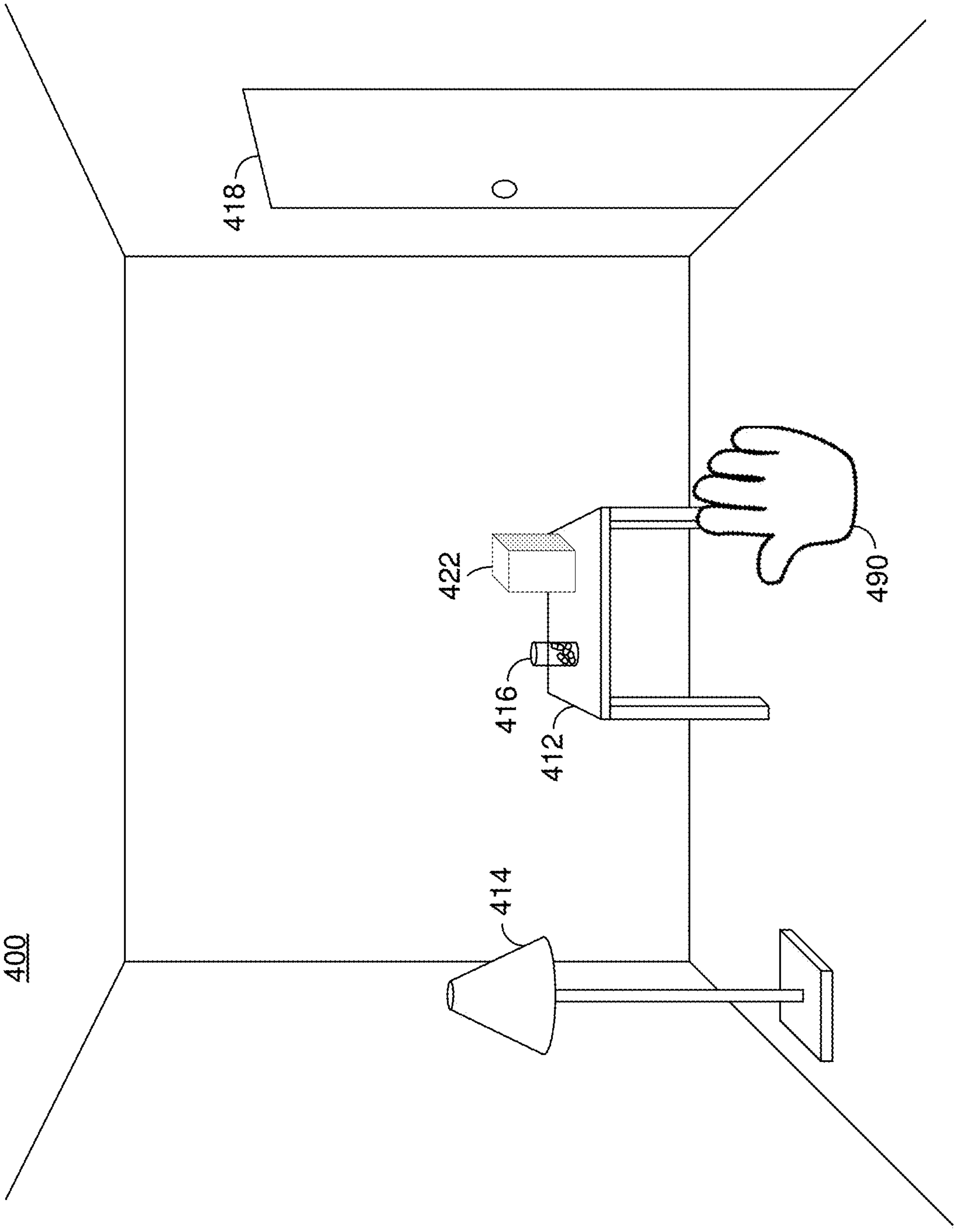

FIG. 4D illustrates the CGR environment 400 of FIG. 4A at a fourth time. At the fourth time, the user has taken the scheduled dose of medication. In response to detecting that the user has taken the scheduled dose of medication, e.g., using the scene camera to detect the dose of medication 417 in the user's hand 490R (e.g., at the third time of FIG. 4C) and/or using an IMU to detect motion of the user's hand 490 towards the user's mouth, the HMD ceases to display the reminder window 431 and the glow 432.

Figure 4E:
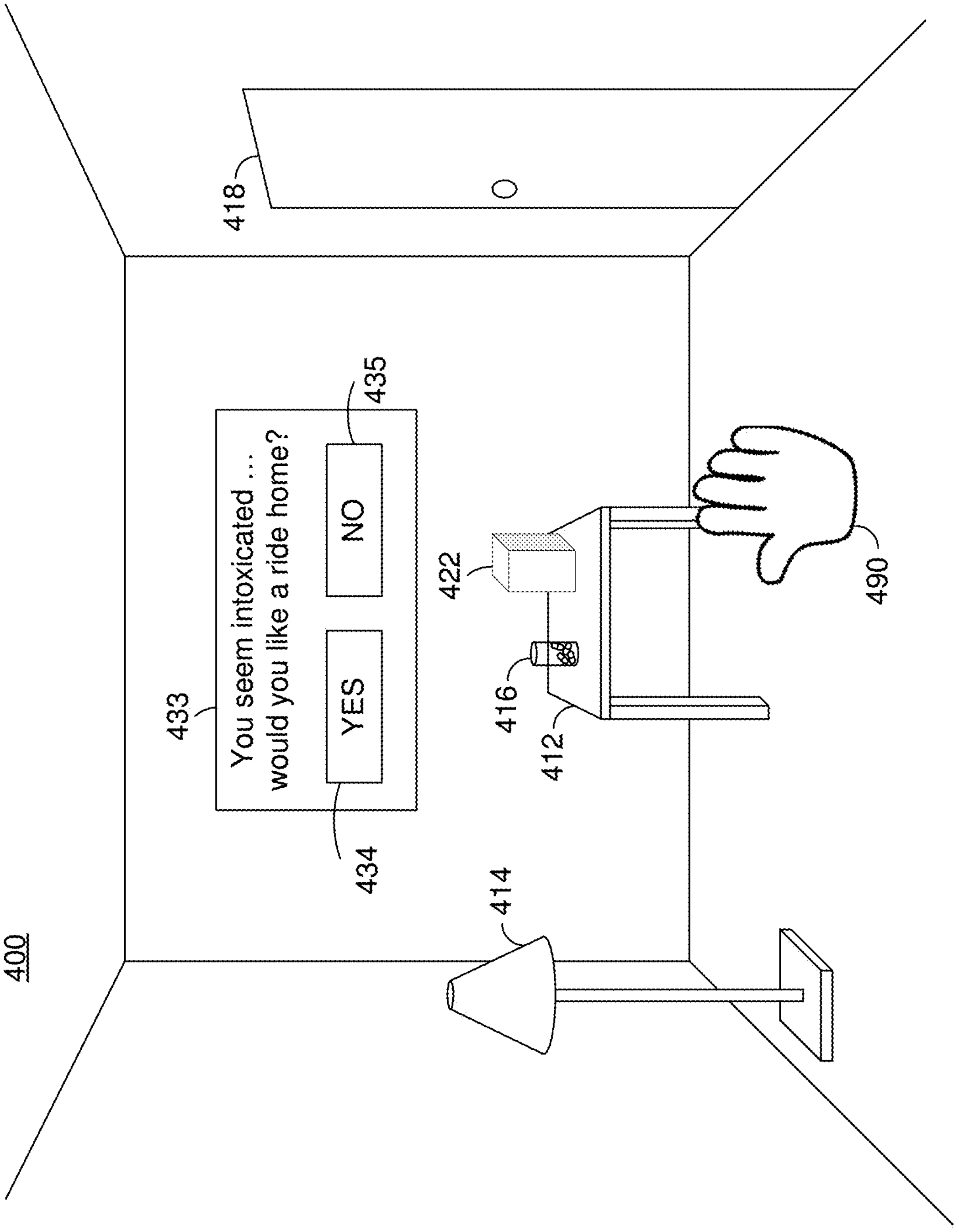

At the fourth time, the HMD detects that the user is intoxicated. For example, using the scene camera and/or an IMU, the HMD detected that the movement of the user's hand 490 (or the user's entire body) to and from the medicine bottle 416 was unsteady. FIG. 4E illustrates the CGR environment 400 of FIG. 4A in response to the HMD detecting that the user is intoxicated.

FIG. 4E illustrates the CGR environment 400 of FIG. 4A at a fifth time. At the fifth time, the CGR environment 400 includes an options window 433 including a yes affordance 434 and a no affordance 435. The options window 433 indicates to the user that the user is intoxicated and presents options for calling a rideshare vehicle (via the yes affordance 434) and dismissing the options window 433 (via the no affordance 435).

Figure 4F:
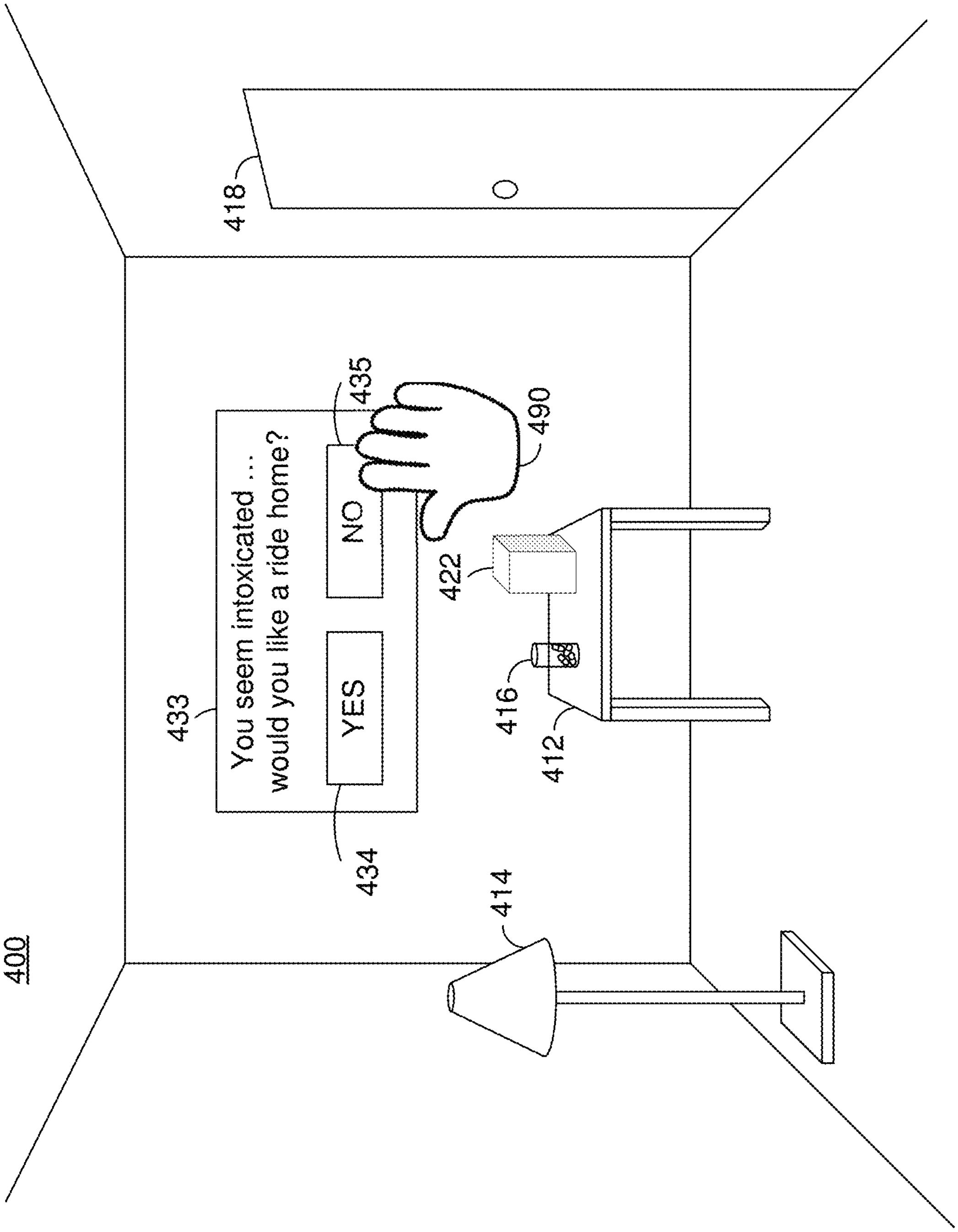

FIG. 4F illustrates the CGR environment 400 of FIG. 4A at a sixth time. At the sixth time, the user's hand 490 is interacting with the no affordance 435 of the options window 433.

Figure 4G:
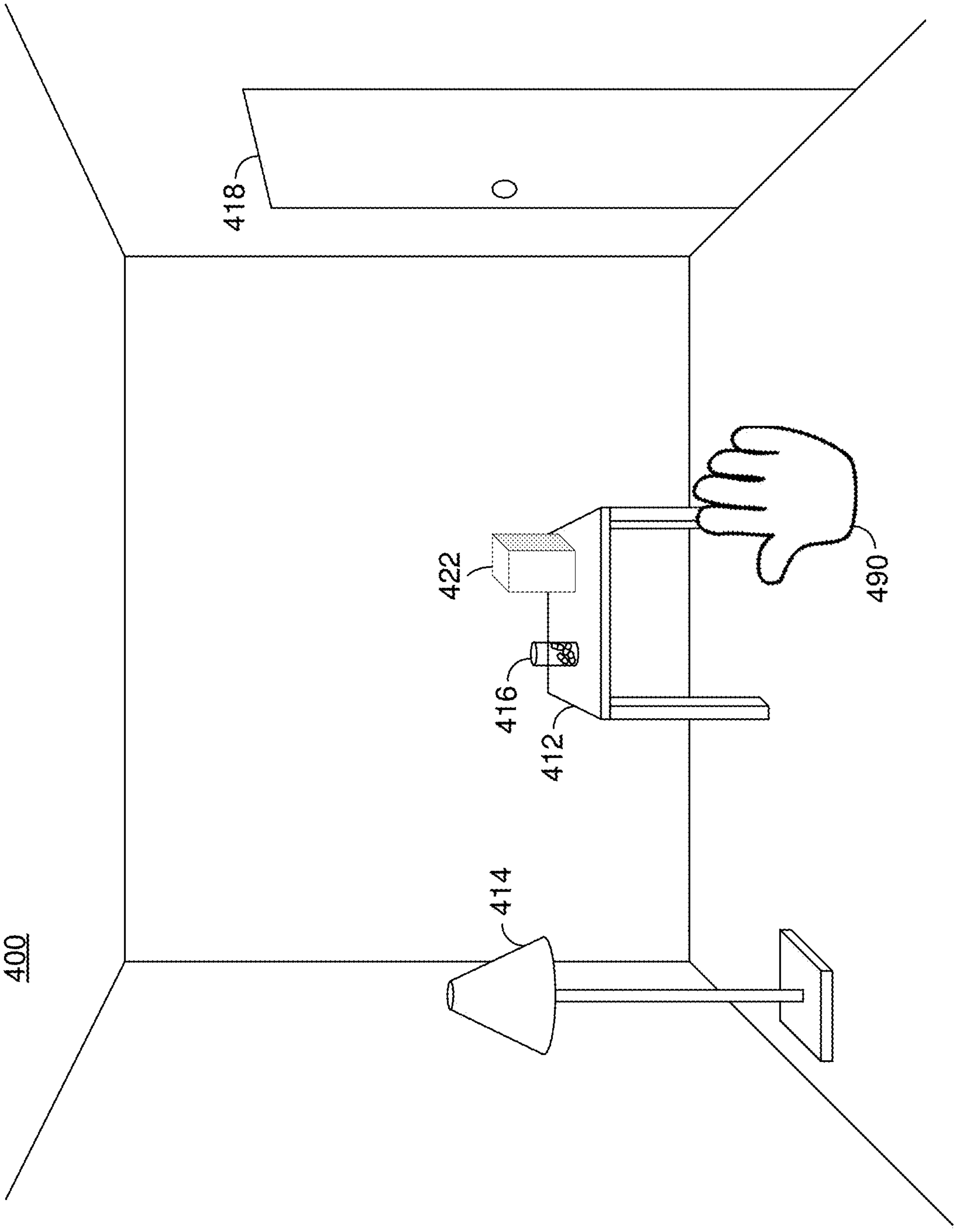

FIG. 4G illustrates the CGR environment 400 of FIG. 4A at a seventh time. At the seventh time, in response to the HMD detecting the user interacting with the no affordance 435, the options window 433 ceases to be displayed.

Figure 4H:
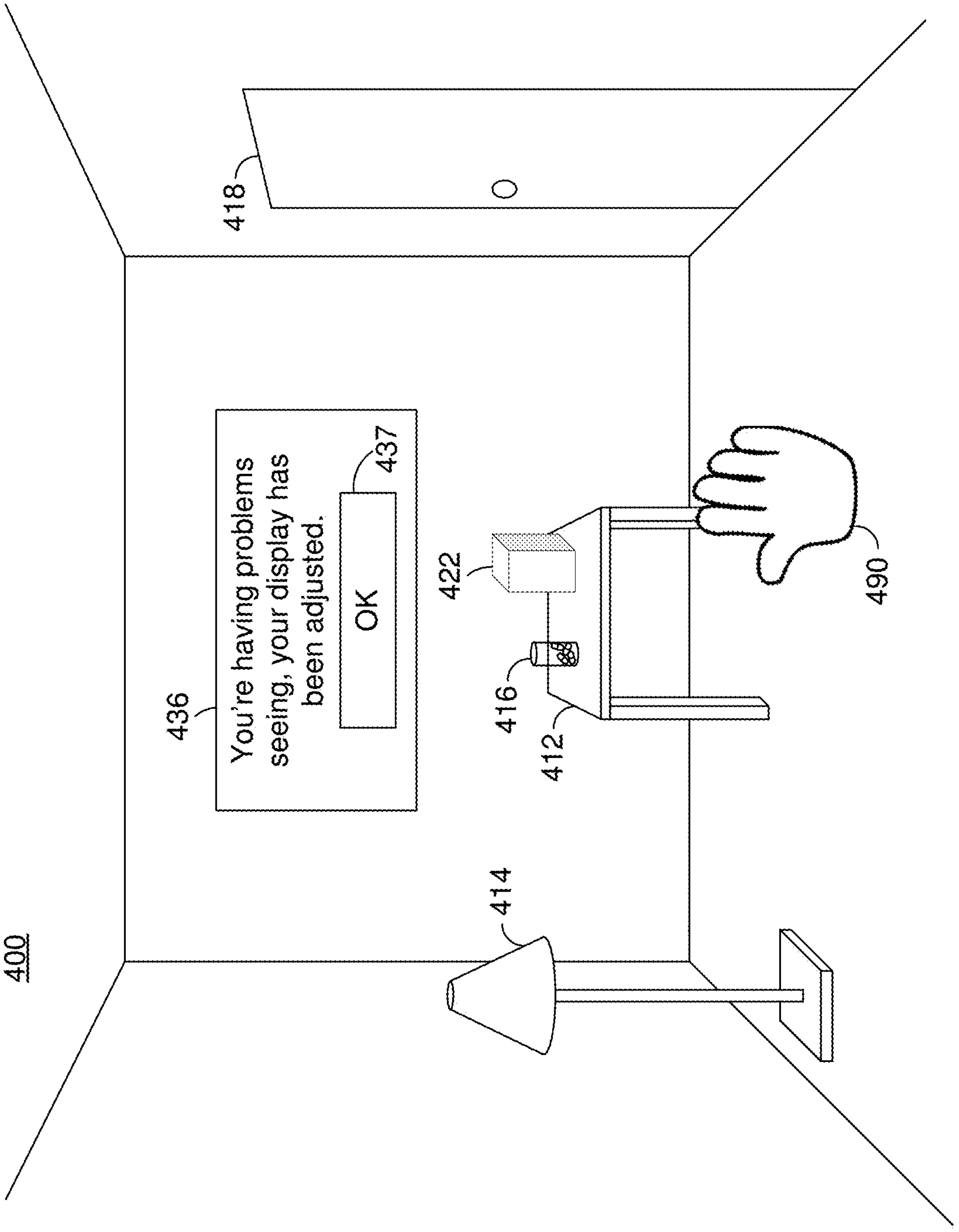

At the seventh time, the HMD detects that the user is vision impaired. For example, using the scene camera and/or an IMU, the HMD detects that the movement of the user's hand 490 to and from the no affordance 435 was imprecise, misaimed, or unsteady. As another example, using an eye tracking camera, the HMD detects that the user is squinting and/or closing one eye to avoid double vision. FIG. 4H illustrates the CGR environment 400 of FIG. 4A in response to the HMD detecting that the user is vision impaired.

FIG. 4H illustrates the CGR environment 400 of FIG. 4A at an eighth time. At the eighth time, the CGR environment 400 is adjusted to be brighter and/or sharper (e.g., the HMD increases the brightness, sharpness, saturation, and/or contrast of the display). At the eighth time, the CGR environment 400 includes a notification window 436 indicating that the CGR environment 400 has been adjusted and including an OK affordance 437. The notification window 436 is dismissed (e.g., ceases to be displayed) in response to the user interacting with the OK affordance 437 or after a threshold amount of time (e.g., 10 seconds).

Figure 4I:
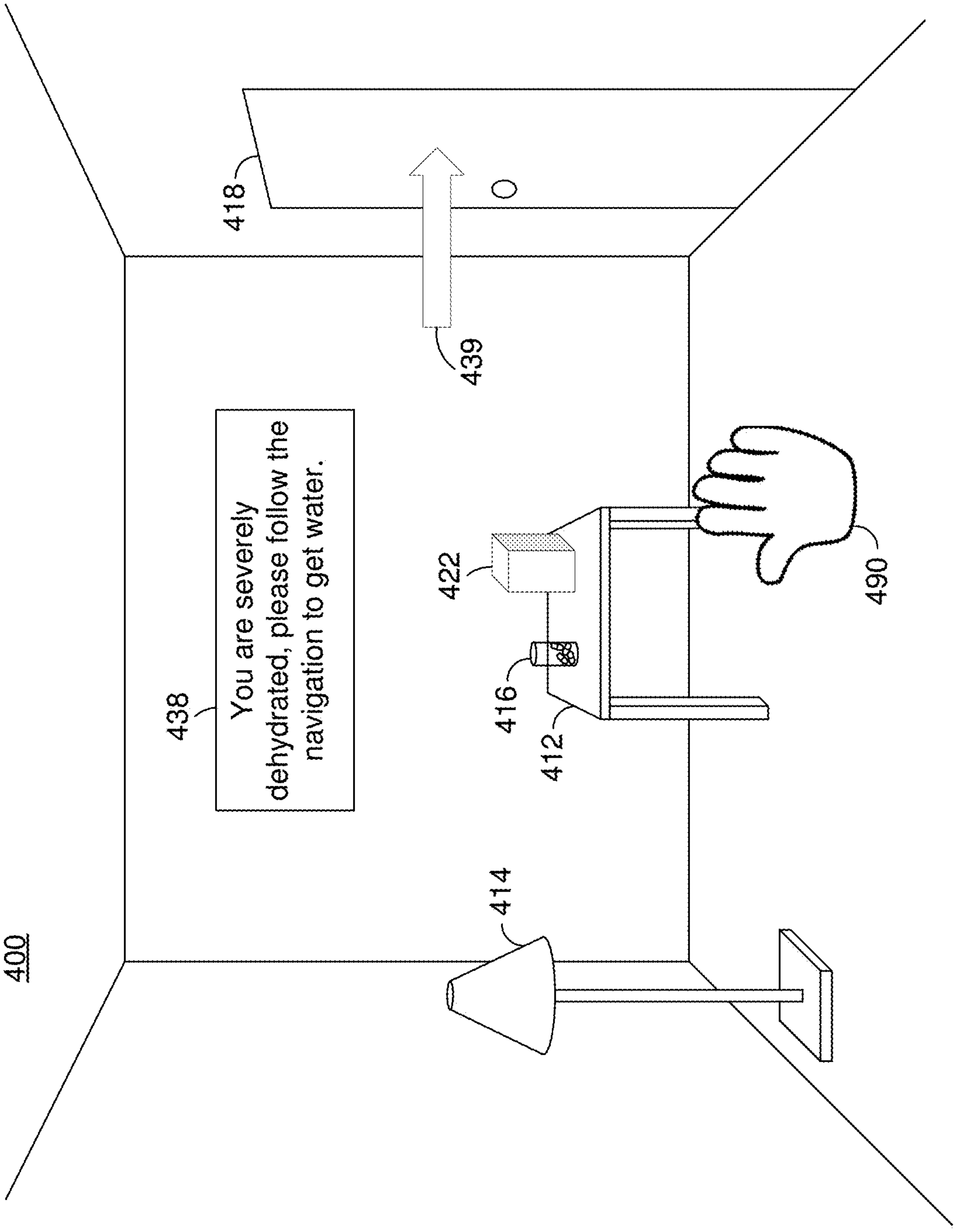

At the eighth time, the HMD detects the user is dehydrated, e.g. using the scene camera to determine water intake, using an IMU to determine dizziness, or using a thermometer, skin sensor, or a breathing monitor. FIG. 4I illustrates the CGR environment 400 of FIG. 4A in response to the HMD detecting that the user is vision impaired.

FIG. 4I illustrates the CGR environment 400 of FIG. 4A at a ninth time. At the ninth time, the CGR environment 400 includes a navigation window 438 indicating that the HMD is navigating the user to water and a navigation arrow 439 (pointing out the door 418) indicating a direction for the user to follow to obtain water.

Figure 5:
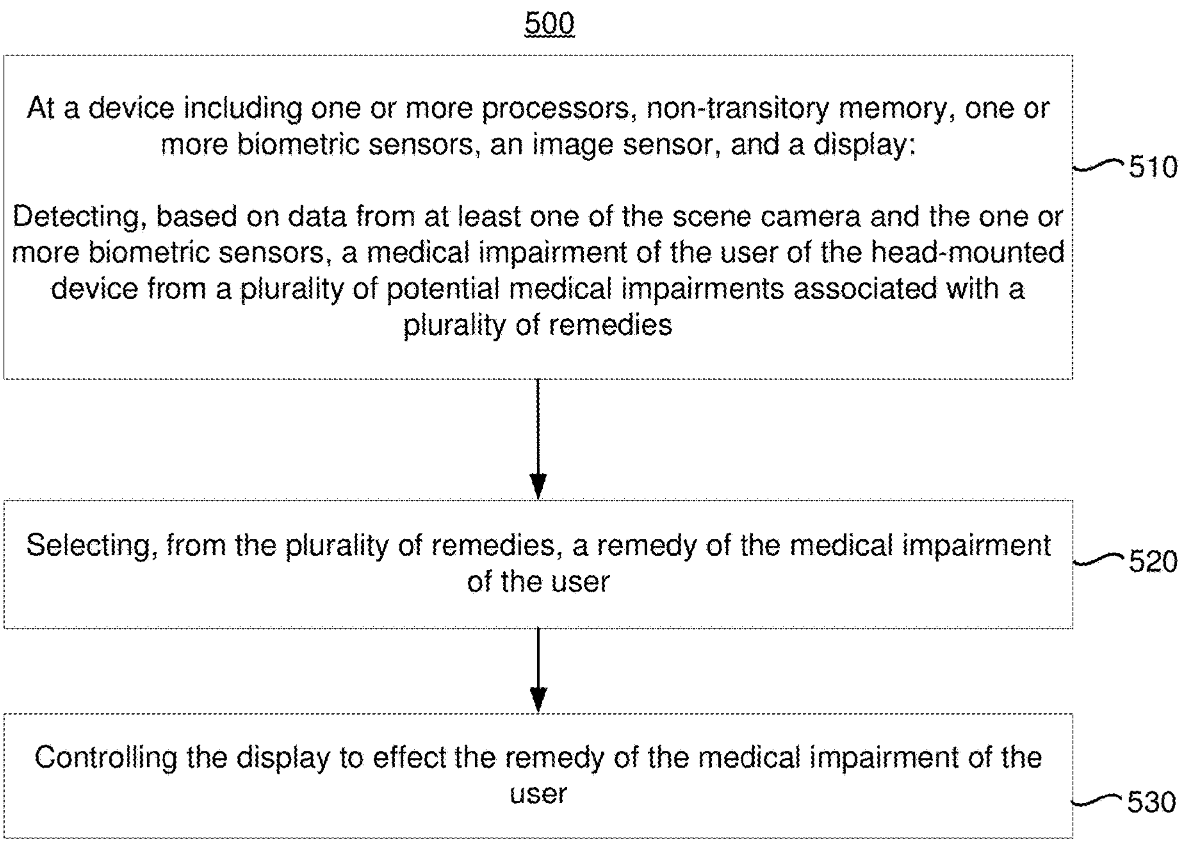
FIG. 5 is a flowchart representation of a method of remedying a medical impairment of a user in accordance with some implementations.

FIG. 5 is a flowchart representation of a method 500 of remedying a medical impairment of a user in accordance with some implementations. In various implementations, the method 500 is performed by a device with one or more processors, non-transitory memory, one or more biometric sensors, an image sensor (e.g., one or more scene cameras), and a display (e.g., the HMD 120B of FIG. 3). In some implementations, the method 500 is performed by processing logic, including hardware, firmware, software, or a combination thereof. In some implementations, the method 500 is performed by a processor executing instructions (e.g., code) stored in a non-transitory computer-readable medium (e.g., a memory).

The method 500 begins, in block 510, with the device detecting, based on data from at least one of the image sensor and the one or more biometric sensors, a medical impairment of a user of the device from a plurality of potential medical impairments associated with a plurality of remedies.

In various implementations, the device detects that the user has hypothermia or hyperthermia using the image sensor to determine a color of the user's skin or a change in the color of the user's skin (e.g., bluish hue indicates hypothermia and/or a reddish hue indicates hyperthermia) and/or one or more biometric sensors, such as a thermometer, a heart rate monitor to determine a heart rate of the user or a change in the heart rate of the user (e.g., increased heart rate indicates hypothermia or hyperthermia), or a breathing monitor to determine a breathing rate of the user or a change in the breathing rate of the user (e.g., rapid breathing indicates hyperthermia or mild hypothermia and/or slowed breathing indicates severe hypothermia).

In various implementations, the device detects that the user is intoxicated or dehydrated using the image sensor to determine a steadiness of the user's movement, either the user's entire body or a portion thereof, such as the hand (e.g., unsteadiness indicates intoxication or dehydration) and/or one or more biometric sensors, such as an IMU to determine a steadiness of the user's movements, a microphone to determine a clarity of the user's speech, a breathalyzer to determine an alcohol content of the user's breath.

In various implementations, the device detects whether a user has failed to take a scheduled dose of medication using the image sensor to detect the user taking (or failing to detect the user taken) the scheduled dose of medication and/or one or more biometric sensors, such as an IMU to detect motion of the user's hand toward the user's mouth or motion of the user's head tilted backward as when swallowing a pill or a microphone to detect a swallowing sound.

In various implementations, the device detects that the user has fallen or is having a seizure using the image sensor to detect a dropping (and/or tilting) of the camera or a shaking of the user's body or a portion thereof (e.g., the user's hands) and/or one or more biometric sensors, such as an IMU to detect a fall or shaking or a heart rate monitor to determine a heart rate of the user or a change in the heart rate of the user (e.g., increased heart rate indicates a fall or seizure).

In various implementations, the device detects that the user is vision impaired using the image sensor to detect objects that the user would be expected to notice but hasn't (e.g., by using an eye tracking camera and related gaze information) or detecting that the user is holding reading material or other object unusually close to the user's face and/or one or more biometric sensors, such as an eye tracking camera to detect a user squinting or closing one eye.

Accordingly, in various implementations, the device detects the medical impairment of the user based on data from the image sensor without being based on data from any of the one or more biometric sensors. In various implementations, the device detects the medical impairment of the user based on data from the one or more biometric sensors without being based on data from the image sensor. In various implementations, the device detects the medical impairment of the user based on data from both the image sensor and the one or more biometric sensors.

The method 500 continues, in block 520, with the device selecting, from the plurality of remedies, a remedy of the medical impairment of the user. In various implementations, each of the plurality of potential medical impairments is associated with a respective remedy and the device selects a respective remedy of the detected medical impairment of the user. For example, in various implementations, in response to detecting that a user has failed to take a scheduled dose of medication, a remedy of taking the scheduled dose of medication is selected (which may be effected by instructing the user to take the scheduled dose of medication). As another example, in response to detecting that the user is dehydrated, a remedy of hydrating the user is selected (which may be effected by performing object detection to find and highlight water bottles, water fountains, or other potable water sources or by directing the user to such a source using the user's location and a map).

In various implementations, at least one of the plurality of potential medical impairments is associated with two or more remedies. The particular remedy may be selected based on other factors, such as time of day or user location.

The method 500 continues, in block 530, with the device controlling the display to effect the remedy of medical impairment of the user.

For example, in various implementations, the device displays an object on the display which is displayed for as long as the medical impairment of the user is detected. In various implementations, the object includes instructions to the user to remedy the medical impairment of the user. For example, in FIG. 4B and FIG. 4C, in response to detecting that the user has failed to take a scheduled dose of medication and until the user has taken the scheduled dose of medication, the CGR environment 400 includes the reminder window 431 indicating that the user is to take the scheduled dose of medication.

As another example, in various implementations, the device displays an options object on the display including a plurality of affordances. For example, in FIG. 4E, in response to detecting that the user is intoxicated, the CGR environment 400 includes the options window 433 including the yes affordance 434 and the no affordance 435.

In various implementations, the options object includes an affordance for dismissing the options object (e.g., the no affordance 435 of FIG. 4E). In various implementations, the options object includes an affordance for opening a phone application to place a phone call (e.g., to an emergency contact or 911), opening a rideshare application to call a car, or opening a navigation application to navigate to a destination (such as a hospital or medical office).

As another example, in various implementations, the device adjusts a parameter of the display, such as a brightness, color, contrast, saturation, sharpness, or zoom level. For example, in FIG. 4H, in response to detecting that the user is vision impaired, the CGR environment 400 is so adjusted.

As another example, in various implementations, the device displays a visual cue associated with particular objects. For example, in FIG. 4B, the CGR environment 400 includes the glow 432 directing the attention of the user to the medicine bottle 416. As another example, in response to detecting that the user is having a depth perception problem, flashing lines are displayed around the contours of an object the user may walk into. As another example, in response to detecting that the user has low light sensitivity, the brightness of particular regions of the display (e.g., surrounding particular objects) is increased. As another example, in response to detecting that the user has slow reflexes, attention is directed to a moving object to assist the user in recognizing an obstacle.

As another example, in various implementations, the device displays a navigational aid directing the user to a location based on the medical impairment. For example, in FIG. 4I, in response to detecting that the user is dehydrated, the CGR environment 400 includes the navigation arrow 439 (pointing out the door 418) indicating a direction for the user to follow to obtain water. In various implementations, the location includes the location of water, the location of first aid, the location of a defibrillator, a doctor's office, an urgent care center, or an emergency room.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" May be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" May be construed to mean "upon determining" or "in response to determining" or "in accordance with a determination" or "upon detecting" or "in response to detecting" that the stated condition precedent is true, depending on the context.

What is claimed is:

1. A method comprising:

at a device including one or more biometric sensors, an image sensor, and a display:

determining, at a first time after a time of a scheduled task and based on data from at least one of the image sensor and the one or more biometric sensors, whether a user of the device has performed the scheduled task;

in accordance with a determination that the user has not performed the scheduled task, initiating, at a second time after the first time, display, on the display, of an indication that the user has not performed the scheduled task, wherein the indication includes a virtual object displayed in association with a real object associated with the scheduled task; and while displaying the indication, in accordance with a determination that the user has performed the scheduled task, ceasing display of the indication that the user has not performed the scheduled task.

2. The method of claim 1, wherein determining whether the user has performed the scheduled task is based on data from the image sensor without being based on data from the one or more biometric sensors.

3. The method of claim 1, wherein determining whether the user has performed the scheduled task is based on data from the one or more biometric sensors without being based on data from the image sensor.

4. The method of claim 1, wherein determining whether the user has performed the scheduled task is based on data from both the image sensor and the one or more biometric sensors.

5. The method of claim 1, wherein the one or more biometric sensors includes an inertial measurement unit (IMU).

6. The method of claim 1, wherein the indication includes a virtual object describing the scheduled task.

7. The method of claim 6, wherein the virtual object includes a dismiss affordance for ceasing to display the virtual object.

8. The method of claim 1, wherein the virtual object is a glow surrounding the real object.

9. The method of claim 1, wherein the one or more biometric sensors include one or more of a heart monitor, a breathing monitor, a thermometer, and an electrodermal monitor.

10. A device comprising:

one or more biometric sensors;

an image sensor;

a display;

a non-transitory memory; and one or more processors to:

determine, at a first time after a time of a scheduled task and based on data from at least one of the image sensor and the one or more biometric sensors, whether a user of the device has performed the scheduled task;

in accordance with a determination that the user has not performed the scheduled task, initiate, at a second time after the first time, display, on the display, of an indication that the user has not performed the scheduled task, wherein the indication includes a virtual object displayed in association with a real object associated with the scheduled task; and while displaying the indication, in accordance with a determination that the user has performed the scheduled task, cease display of the indication that the user has not performed the scheduled task.

11. The device of claim 10, wherein the one or more biometric sensors includes an inertial measurement unit (IMU).

12. The device of claim 10, wherein the indication includes a virtual object describing the scheduled task.

13. The device of claim 12, wherein the virtual object includes a dismiss affordance for ceasing to display the virtual object.

14. The device of claim 10, wherein the virtual object is a glow surrounding the real object.

15. The device of claim 10, wherein determining whether the user has performed the scheduled task is based on data from both the image sensor and the one or more biometric sensors.

16. The device of claim 10, wherein the one or more biometric sensors include one or more of a heart monitor, a breathing monitor, a thermometer, and an electrodermal monitor.

17. A non-transitory computer-readable medium having instructions encoded thereon which, when executed by a device including one or more biometric sensors, an image sensor, and a display, cause the device to:

determine, at a first time after a time of a scheduled task and based on data from at least one of the image sensor and the one or more biometric sensors, whether a user of the device has performed the scheduled task; and in accordance with a determination that the user has not performed the scheduled task, initiate display, on the display, of an indication that the user has not performed the scheduled task, wherein the indication includes a virtual object displayed in association with a real object associated with the scheduled task; and while displaying the indication, in accordance with a determination that the user has performed the scheduled task, cease display of the indication that the user has not performed the scheduled task.

18. The non-transitory computer-readable medium of claim 17, wherein the indication includes a virtual object describing the scheduled task.

19. The non-transitory computer-readable medium of claim 17, wherein determining whether the user has performed the scheduled task is based on data from both the image sensor and the one or more biometric sensors.

20. The non-transitory computer-readable medium of claim 17, wherein the one or more biometric sensors include one or more of a heart monitor, a breathing monitor, a thermometer, and an electrodermal monitor.

* * * * *